Sept. 16, 1958 R. F. CURTIS Plant Pat. 1,750
ROSE PLANT
Filed Aug. 29, 1957
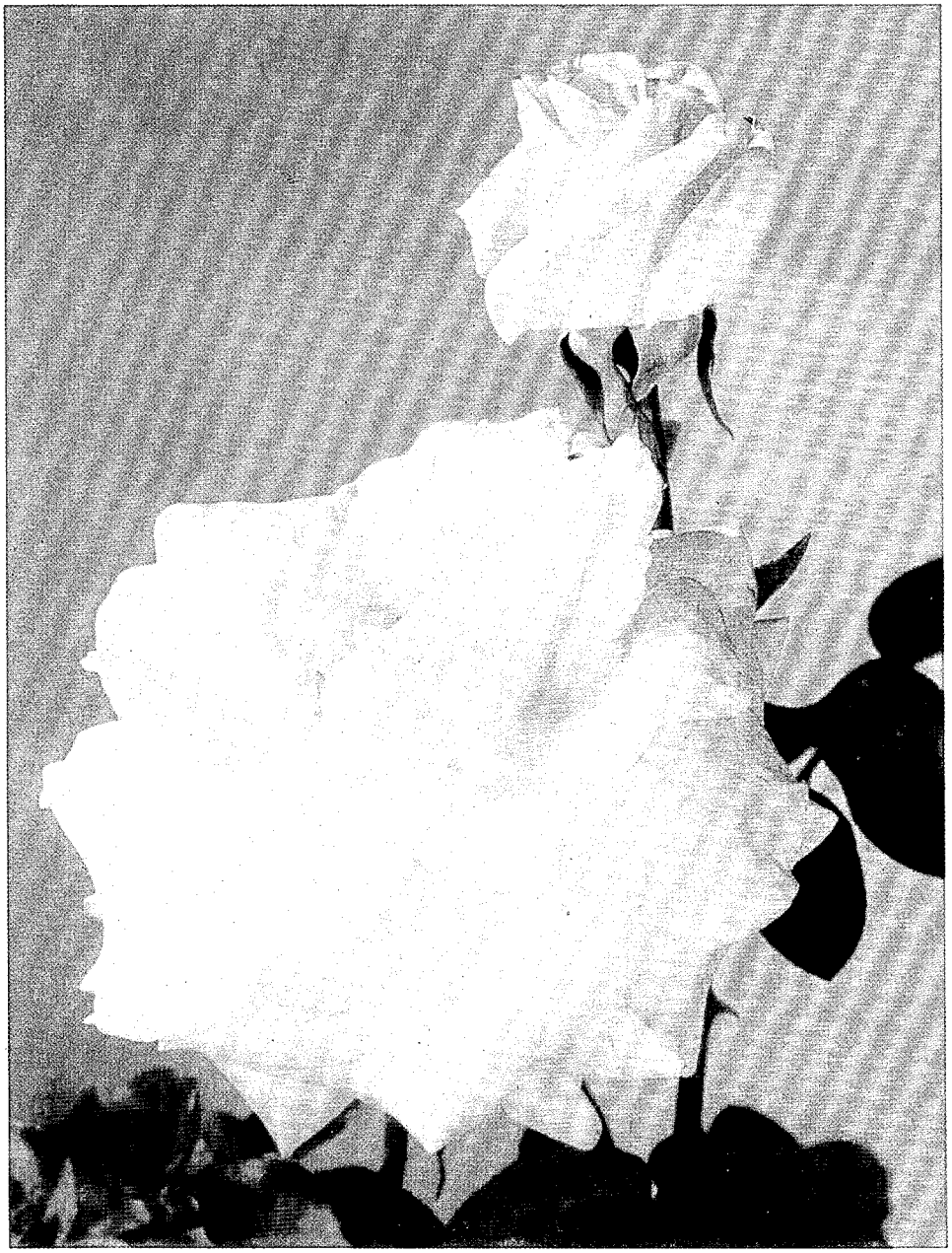
Inventor.
R. F. Curtis
By: Robert Cobb
Attorneys.

United States Patent Office

Plant Pat. 1,750
Patented Sept. 16, 1958

1,750

ROSE PLANT

Raleigh F. Curtis, Torrance, Calif., assignor to Armstrong Nurseries, Inc., Ontario, Calif., a corporation of California Application August 29, 1957, Serial No. 681,154

1 Claim. (Cl. 47—61)

The present invention relates to a new and distinct variety of rose plant of the hybrid tea class, which originated as a bud sport of the variety "Peace" (Plant Patent No. 591).

The new variety was discovered by me on a plant of "Peace" which was being grown by me on my cultivated property at Torrance, California. At the time of my discovery aforementioned, my attention was attracted to the same by the fact that the plant bore flowers which had a color substantially different from the normal color of the flowers of the parent, the latter normally being Lemon Yellow and Cream, edged with Rose Pink, whereas the flowers observed by me were Light Pink in color. Upon closer examination of the plant, I found that it had sported, and I thereupon took steps to preserve the sport, keep it under observation and later asexually reproduce the same. My observations and asexual reproductions, as performed by me by budding at Torrance, California, fully confirmed the new flower color characteristics of the sport and conclusively established that these characteristics come true to form and are transmissible through succeeding propagations.

Other than the difference in the color of the flowers as noted in the foregoing, the new sport is substantially identical to its parent, "Peace," and accordingly, it is unnecessary to describe the sport in complete detail, since it conforms to the description appearing in Plant Patent No. 591, dated June 15, 1943, to which reference may be readily had.

For convenience, the accompanying drawing shows typical specimens of the flowers of the new sport in different stages of development and as depicted in color as nearly true as it is reasonably possible to make the same in a color illustration of this character.

The following is a detailed description of the flower color, from which the distinctions from the parent variety and from all other varieties of which I am aware, will become fully apparent, with color nomenclature in accordance with Robert F. Wilson's Horticultural Colour Chart:

*Flower*

(Observations made from specimens grown outdoors at Ontario, California, in the month of November.)

As calyx breaks:

*Color.*—Near Claret Rose, Plate 021/1, pg. 109.

Newly opened flower:

*Color.*—Outer petal:—outside surface—near Camellia Rose, Plate 622/3, pg. 148, fading toward base, and with attachment at base near Empire Yellow, Plate 603, pg. 66; inside surface—near Camellia Rose, Plate 622/3, pg. 148, fading toward base, and with attachment at base near Empire Yellow, Plate 603, pg. 66. Intermediate petal: outside surface—between Camellia Rose, Plate 622/2, pg. 148 and Camellia Rose, Plate 622/3, pg. 148, with small area at base near attachment near Empire Yellow, Plate 603/2, pg. 66; inside surface—between Camellia Rose, Plate 622/2, pg. 148, and Camellia Rose, Plate 622/3, pg. 148, with small area at base near attachment near Empire Yellow, Plate 603/2, pg. 66. Inner petal: outside surface—near Camellia Rose, Plate 622/2, pg. 148, with small area at base near attachment near Empire Yellow, Plate 603/2, pg. 66; inside surface—near Camellia Rose, Plate 622/1, pg. 148, with small area at base near attachment near Empire Yellow, Plate 603, pg. 66.

Three-days open flower:

*Color.*—Outer petal: outside surface—near Camellia Rose, Plate 622/3, pg. 148, fading toward base; inside surface—near Camellia Rose, Plate 622/3, pg. 148, fading toward base, and with small area at base near attachment near Empire Yellow, Plate 603/2, pg. 66. Inner petal: outside surface—between Camellia Rose, Plate 622/2, pg. 148 and Camellia Rose, Plate 622/3, pg. 148; inside surface—between Camellia Rose, Plate 622/2, pg. 148 and Camellia Rose, Plate 622/3, pg. 148.

General color effect:

*Newly opened flower.*—Between Camellia Rose, Plate 622/3, pg. 148 and Camellia Rose, Plate 622/2, pg. 148.

*Three-days open.*—Near Camellia Rose, Plate 622/3, pg. 148.

I claim:

A new and distinct variety of rose plant of the hybrid tea class, substantially as herein shown and described, characterized particularly as to novelty by its general similarity to its parent variety "Peace" (Plant Patent No. 591), but being essentially distinguished therefrom by the Light Pink general color tonality of its flowers.

No references cited.